(12) United States Patent
Mann et al.

(10) Patent No.: US 12,023,457 B2
(45) Date of Patent: Jul. 2, 2024

(54) SUPPORT STRUCTURES FOR DRAINAGE TUBES

(71) Applicant: C. R. Bard, Inc., Franklin Lakes, NJ (US)

(72) Inventors: Gregory Mann, McDonough, GA (US); Rodrigo Fernandez, Conroe, TX (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 0 days.

(21) Appl. No.: 17/180,436

(22) Filed: Feb. 19, 2021

(65) Prior Publication Data

US 2021/0260350 A1    Aug. 26, 2021

Related U.S. Application Data

(60) Provisional application No. 62/979,241, filed on Feb. 20, 2020.

(51) Int. Cl.
  *A61M 27/00*    (2006.01)
(52) U.S. Cl.
  CPC ..... *A61M 27/00* (2013.01); *A61M 2205/0216* (2013.01); *A61M 2205/0266* (2013.01)
(58) Field of Classification Search
  CPC .......... A61M 27/00; A61M 2205/0216; A61M 2205/0266; A61M 27/008; A61M 25/00138; A61M 25/00144; A61M 25/0012; A61M 2025/0004; A61M 2025/0681

See application file for complete search history.

(56) References Cited

U.S. PATENT DOCUMENTS

| | | | | |
|---|---|---|---|---|
| 6,082,583 | A * | 7/2000 | Bussell | ..... A61J 9/00 224/407 |
| 10,857,025 | B2 | 12/2020 | Davis et al. | |
| 2007/0225688 | A1 | 9/2007 | Goodwin | |

(Continued)

FOREIGN PATENT DOCUMENTS

| | | |
|---|---|---|
| WO | 2004056414 A1 | 7/2004 |
| WO | 2007/122174 A1 | 11/2007 |
| WO | 2018/075464 A1 | 4/2018 |

OTHER PUBLICATIONS

PCT/US2021/014935 filed Jan. 25, 2021 International Search Report and Written Opinion dated Jun. 10, 2021.

*Primary Examiner* — Adam Marcetich
*Assistant Examiner* — Rachel O'Connell
(74) *Attorney, Agent, or Firm* — Rutan & Tucker LLP

(57) ABSTRACT

Embodiments are directed to support structures for drainage tubes to relax dependent loops and mitigate fluid pooling. Embodiments include support structures configured to receive an elastic tube and impart rigid or malleable properties thereon. These properties allow a clinician to position the tube to provide a consistent negative incline. Embodiments of support structures include an interlocking segmented tube, a bi-stable or mono-stable support structure, a jacket support structure, or a magnet support structure. Embodiments further include a malleable wire disposed within a wall of an elastic tube, or portions of a tube displaying differing elastic, malleable, or rigid properties. Embodiments also include magnetic peristalsis devices configured to urge fluid through a tube lumen.

10 Claims, 10 Drawing Sheets

(56) References Cited

U.S. PATENT DOCUMENTS

| | | | |
|---|---|---|---|
| 2012/0184944 A1* | 7/2012 | Tomes | A61F 5/4404 |
| | | | 604/544 |
| 2016/0109046 A1* | 4/2016 | Lee | F16L 9/22 |
| | | | 285/261 |
| 2018/0368664 A1* | 12/2018 | Nagda | A61B 1/0051 |
| 2019/0209351 A1* | 7/2019 | Mangiardi | A61B 17/7258 |
| 2019/0321588 A1* | 10/2019 | Burnett | A61M 1/0001 |
| 2019/0358438 A1* | 11/2019 | Fortune | A61M 27/00 |
| 2020/0008820 A1* | 1/2020 | Aboytes | A61B 17/12109 |
| 2020/0015876 A1* | 1/2020 | Chou | A61B 5/068 |
| 2022/0339023 A1 | 10/2022 | Davis et al. | |
| 2023/0091531 A1 | 3/2023 | Tourchak et al. | |

\* cited by examiner

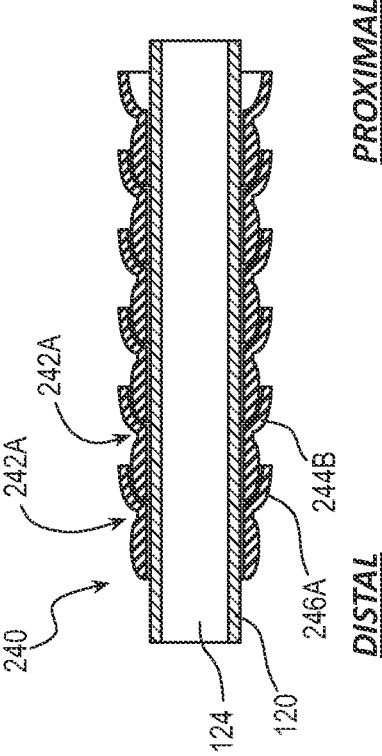
FIG. 2A
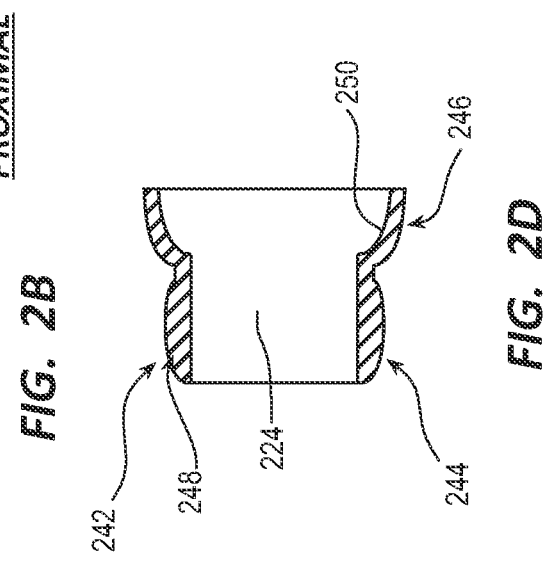
FIG. 2B
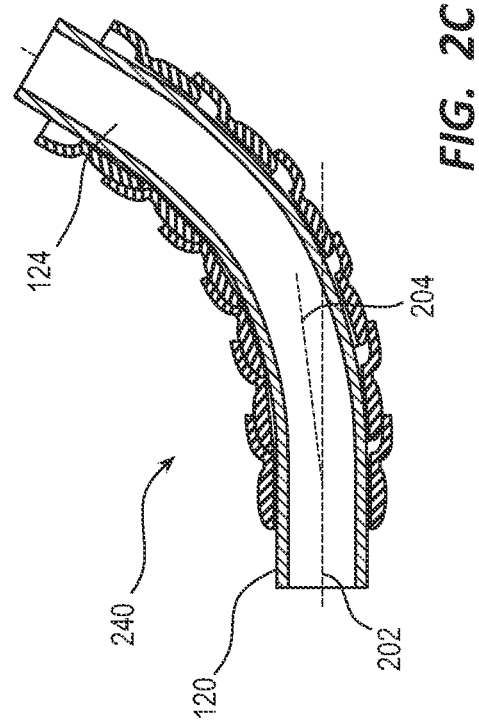
FIG. 2C
FIG. 2D

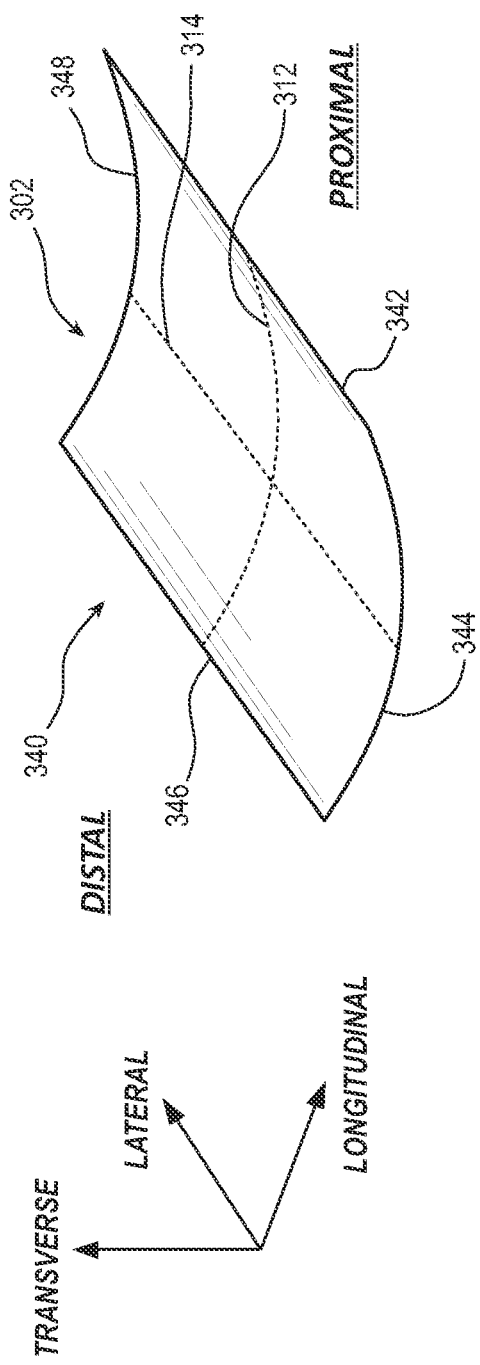
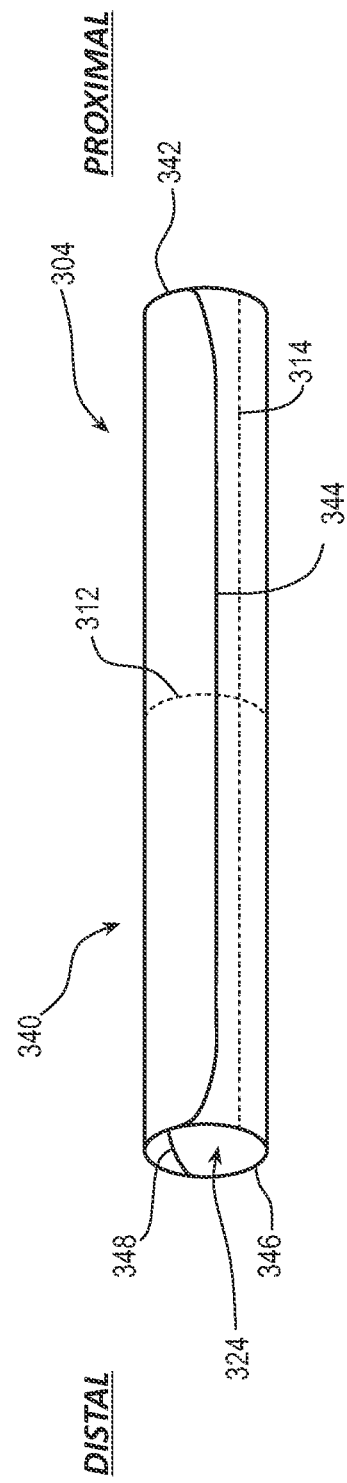
FIG. 3A
FIG. 3B

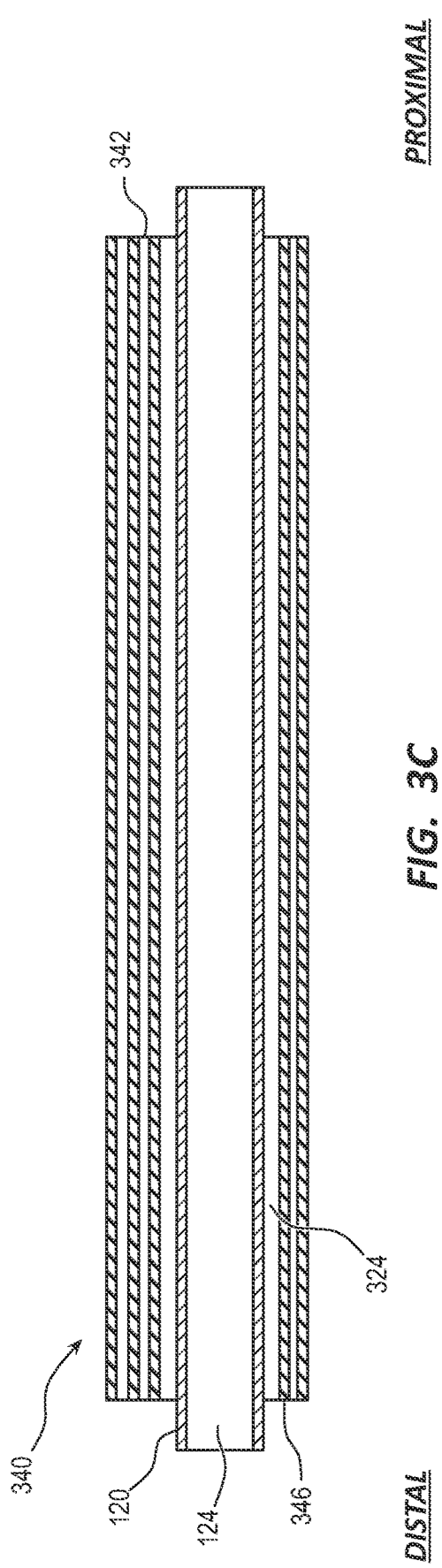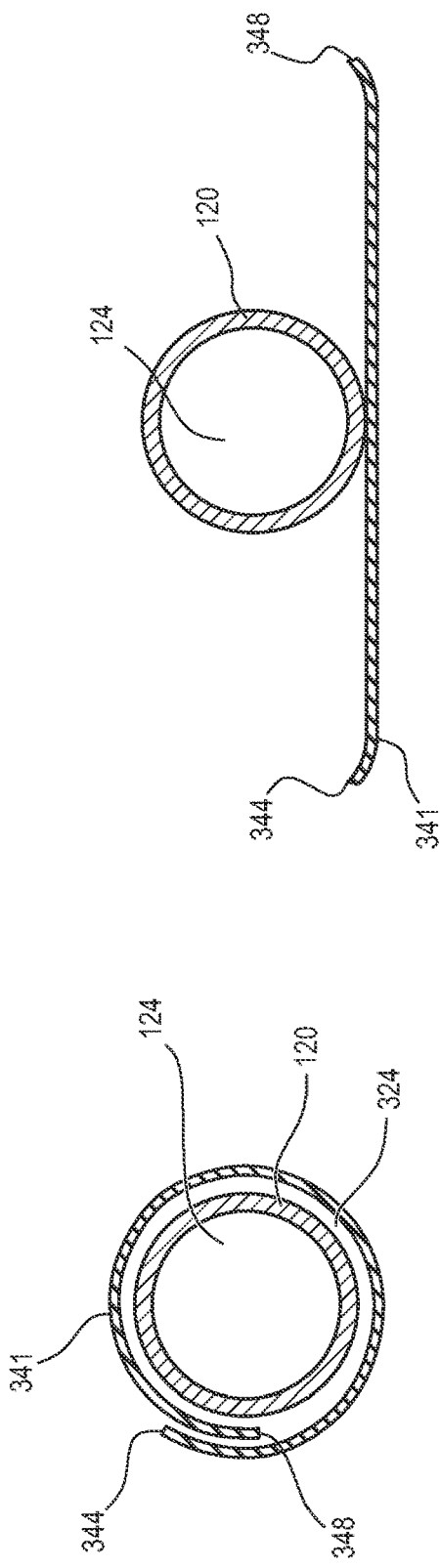

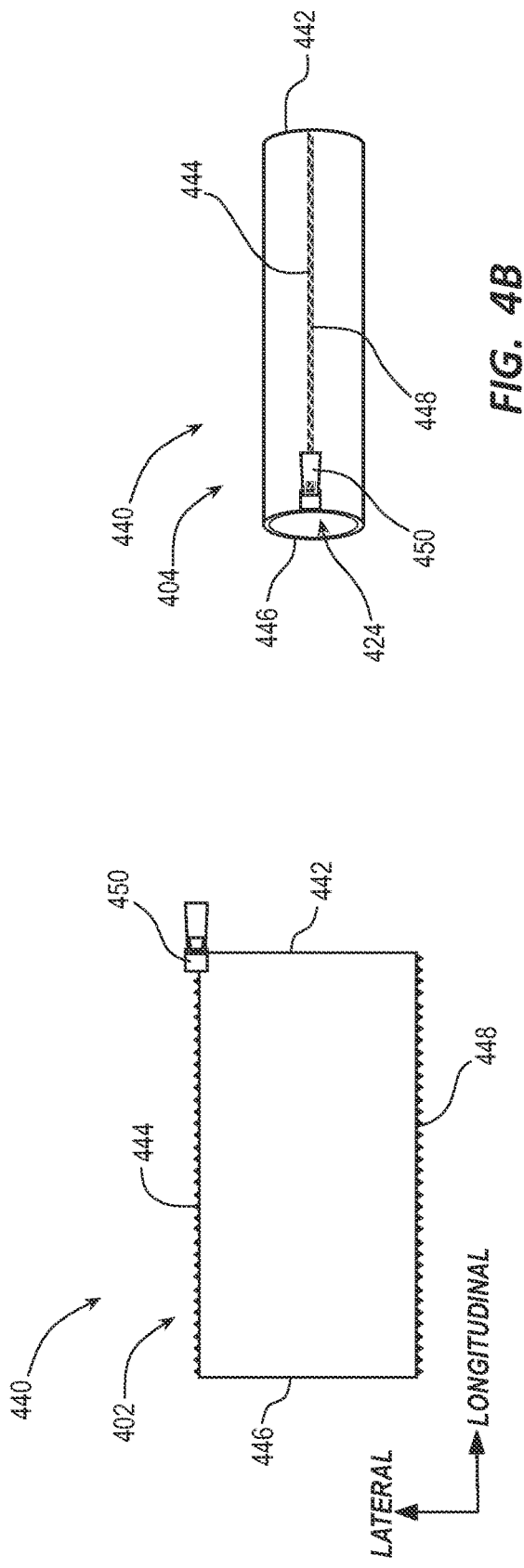
FIG. 4A
FIG. 4B
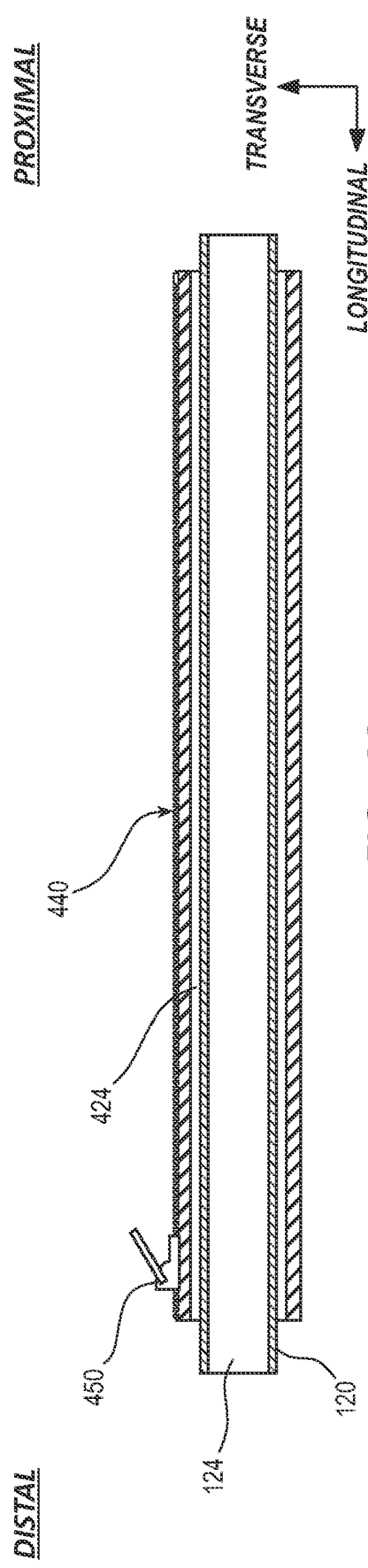
FIG. 4C

SUPPORT STRUCTURES FOR DRAINAGE TUBES

PRIORITY

This application claims the benefit of priority to U.S. Provisional Application No. 62/979,241, filed Feb. 20, 2020, which is incorporated by reference in its entirety into this application.

SUMMARY

Briefly summarized, embodiments disclosed herein are directed to systems and methods of supporting drainage tubes to mitigate pooling of fluid therein and relax dependent loops. Dependent loops within drainage tubes can cause fluid to pool, or result in retrograde flow, within drainage tubes. Fluid pooling or retrograde flow can cause various complications. For example, urine pooling can be a source of catheter associated urinary tract infection ("CAUTI") causing agents such as bacteria, microbes, and the like. Hospital Acquired Infections ("HAI"), such as CAUTI, are detrimental to the patient, and also incur extra costs in treating these additional complications.

Disclosed herein is a drainage system, including a drainage tube, and a support structure defining a central lumen configured to receive a portion of the drainage tube, the support structure including a plurality of segments, a first segment of the plurality of segments engaging an adjacent segment such that the first segment is positionable relative to the adjacent segment to define a shape of the central lumen, and to impart the shape on the portion of the drainage tube disposed therein.

In some embodiments, the plurality of segments are positionable such that the first segment is positioned from a first position to a second position, and remains in the second position until the first segment is repositioned. Each segment of the plurality of segments includes a ball portion and a socket portion, the socket portion of a first segment is configured to engage the ball portion of the adjacent segment in a friction fit engagement. An inner surface of the central lumen engages an outer surface of the drainage tube and is configured to allow the support structure to be slidable along an axis of the drainage tube to a position, and remain at the position until repositioned. An axis of the first segment can be positioned at an angle, relative to an axis of the adjacent segment, of between 0° and 45°. A distal end of the drainage tube is in fluid communication with a catheter and a proximal end of the drainage tube is in fluid communication with a collection container, the drainage tube configured to drain a fluid from the body of a patient.

Also disclosed is a system for draining fluid including, an elastic tube defining a lumen and extending from a distal end to a proximal end, and a support structure including a substantially rectangular sheet of material and configured to transition between an open position for receiving a portion of the elastic tube, and a closed position encircling the portion of the elastic tube to impart rigid properties on the portion of the elastic tube.

In some embodiments, the support structure is formed of a mono-stable material biased towards the closed position and wherein a first lateral edge and a second lateral edge are straight, and wherein a proximal edge and a distal edge are curved. The support structure is formed of a bi-stable material including two resting states, the open position includes a first resting state and the closed position includes a second resting state, and wherein in the open position a proximal edge and a distal edge are straight, and a first lateral edge and a second lateral edge are curved, and wherein in the closed position a proximal edge and a distal edge are curved, and a first lateral edge and a second lateral edge are straight. Transitioning the support structure from the first resting state to the second resting state includes flexing the support structure through a plane that extends perpendicular to a plane defined by the support structure in the first resting state. The support structure in the closed position encircles the portion of the elastic tube through more than 360°.

In some embodiments, the proximal edge overlaps a distal edge when the support structure is in the second resting state. The support structure is formed of a synthetic material and includes a fastener configured to secure a first lateral edge to a second lateral edge in the closed position. The synthetic material is neoprene and the fastener is a zip fastener. The support structure in the closed position defines a lumen, an inner surface of the support structure lumen engages an outer surface of the elastic tube to fit tightly about the elastic tube and impart rigid properties thereon without compromising the patency of the lumen of the elastic tube.

Also disclosed is a fluid tubing system including, an elastic tube extending from a proximal end to a distal end and defining a fluid lumen, and a malleable spine extending through a wall of the tube and configured to impart malleable properties on to the elastic tube.

In some embodiments, the spine extends through the wall of the tube and encircles the fluid lumen in a helical shape. In some embodiments, the fluid tubing system further includes two or more malleable spines disposed either side of the fluid lumen, the malleable spine including a malleable material including one of a metal, an alloy, a plastic, a polymer, or nitinol. In some embodiments, the fluid tubing system further includes a support structure lumen disposed within a wall of the elastic tube and the malleable spine is disposed therein. The distal end of the fluid lumen is in fluid communication with a catheter and the proximal end of the fluid lumen is in fluid communication with a collection container, the elastic tube is configured to drain a fluid from the body of a patient.

Also disclosed is a method of supporting an elastic drainage tube including, engaging a support structure with a portion of the elastic tube, transitioning the support structure from a first position to a second position, the support structure remaining in the second position until repositioned, imparting the second position of the support structure to the elastic tube, the elastic tube remaining in the second position until the support structure is repositioned.

In some embodiments, the support structure includes a segmented tube including a plurality of interlocking segments, a first segment of the plurality of interlocking segments engaging an adjacent segment in a friction fit such that the first segment is designed to transition from the first position to the second position. The support structure includes a bi-stable sheet and wherein the first position is an extended resting state, and the second position is a cylindrical resting state, the support structure encircling the elastic tube in the second position. The support structure includes a sheet of synthetic material and wherein the first position is an open position, and the second position is a closed position where a first lateral edge is secured to a second lateral edge, the support structure encircling the elastic tube in the second position.

Also disclosed is a fluid collection system including, a catheter, a collection container, and a tube providing fluid communication between the catheter and the container including, a support structure portion including a first material displaying one of a rigid or a malleable property, and a second portion including a second material displaying one of a malleable or an elastic property.

In some embodiments, the first material includes one of a plastic, a polymer, a high density polyethylene (HDPE), or nylon. The second material includes one of a plastic, a polymer, Polyvinyl chloride (PVC), silicone, or rubber.

DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIG. 2A shows a perspective view of a segmented support structure, in accordance with embodiments disclosed herein.

FIGS. 2B-2C show a longitudinal cross-sectional view of a segmented support structure, in accordance with embodiments disclosed herein.

FIG. 2D shows a longitudinal cross-sectional view of a segment of the segmented support structure shown in FIGS. 2A-2C, in accordance with embodiments disclosed herein.

FIG. 3A shows a perspective view of a bi-stable support structure in an extended resting state, in accordance with embodiments disclosed herein.

FIG. 3B shows a perspective view of a bi-stable support structure in a cylindrical resting state, in accordance with embodiments disclosed herein.

FIG. 3C shows a longitudinal cross-sectional view of a bi-stable support structure in a cylindrical resting state, in accordance with embodiments disclosed herein.

FIG. 3D shows a lateral cross-sectional view of a mono-stable support structure in a cylindrical resting state, in accordance with embodiments disclosed herein.

FIG. 3E shows a lateral cross-sectional view of a mono-stable support structure in an open position, in accordance with embodiments disclosed herein.

FIG. 4A shows a jacket support structure in an open position, in accordance with embodiments disclosed herein.

FIG. 4B shows a jacket support structure in a closed position, in accordance with embodiments disclosed herein.

FIG. 4C shows a longitudinal cross-sectional view of a jacket support structure in a closed position, in accordance with embodiments disclosed herein.

DESCRIPTION

Figures 1A, 1B:
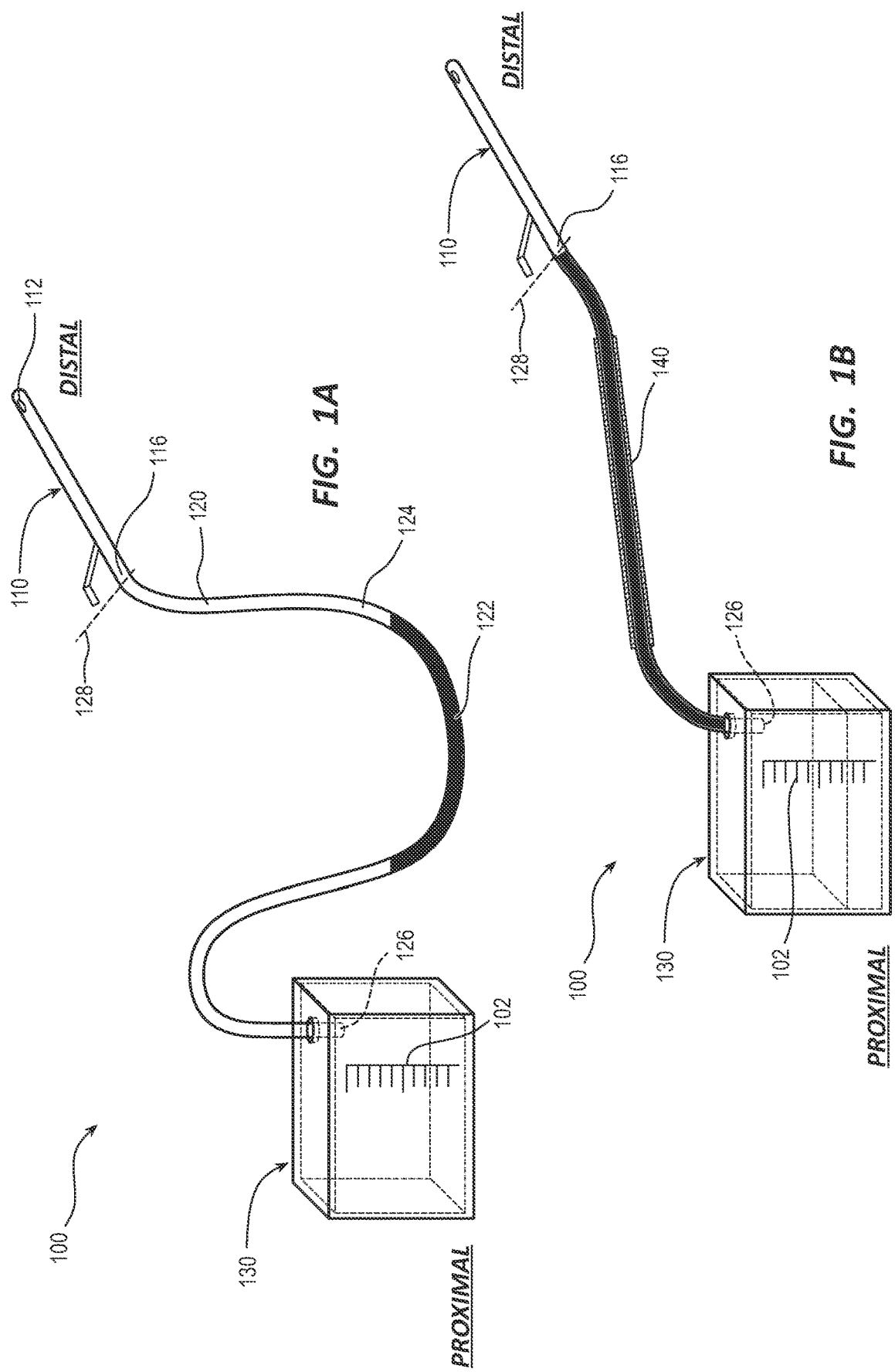
FIG. 1A shows an exemplary catheter and fluid collection system, in accordance with embodiments disclosed herein.
FIG. 1B shows an exemplary catheter and fluid collection system including a support structure to relax dependent loops, in accordance with embodiments disclosed herein.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal end portion, or the proximal length of the catheter can include the proximal end of the catheter; however, the proximal portion, the proximal end portion, or the proximal length of the catheter need not include the proximal end of the catheter. That is, unless context suggests otherwise, the proximal portion, the proximal end portion, or the proximal length of the catheter is not a terminal portion or terminal length of the catheter.

With respect to "distal," a "distal portion" or a "distal end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal end portion, or the distal length of the catheter can include the distal end of the catheter; however, the distal portion, the distal end portion, or the distal length of the catheter need not include the distal end of the catheter. That is, unless context suggests otherwise, the distal portion, the distal end portion, or the distal length of the catheter is not a terminal portion or terminal length of the catheter.

As used herein, the term "elastic" properties refers to the mechanical properties of deforming when a force is applied and then returning to its original shape when the force is removed. The term "malleable" properties includes deforming, without rupturing, when a force is applied and remaining in the deformed state when the force is removed. To assist in the description of embodiments described herein, as shown in FIG. 3A, a longitudinal axis extends substantially parallel to an axial length of the tube 120. A lateral axis extends normal to the longitudinal axis, and a transverse axis extends normal to both the longitudinal and lateral axes. Unless defined otherwise, all technical and scientific terms used herein have the same meaning as commonly understood by those of ordinary skill in the art.

FIG. 1 shows an exemplary fluid collection system 100, which generally includes a catheter 110, a drainage tube ("tube") 120, and a collection container ("container") 130. Exemplary catheters 110 include indwelling catheters, Foley catheters, balloon catheters, peritoneal drainage catheters, or the like, and are configured to be inserted into an orifice within the body of a patient to drain a fluid therefrom. In an embodiment, the catheter 110 can be inserted through the urethra and into a bladder of a patient. The catheter 110 includes an eyelet 112 that provides fluid communication with a lumen of the catheter 110, and is configured to drain a fluid, e.g. urine.

The tube 120 extends from a distal end 128 to a proximal end 126 to define an axial length, and defines a lumen 124. The distal end 128 of the tube 120 is configured to engage a proximal 116 end of the catheter 110. The tube 120 provides fluid communication between the lumen of the catheter 110 and the collection container 130. The tube 120 can be formed of rubber, plastic, polymer, silicone, or similar suitably compliant material. The collection container 130 can include a rigid container, a flexible collection bag, or similar suitable container for receiving a fluid, e.g. urine, drained from the catheter 110. In an embodiment, the container 130 includes graduated markings 102 for measuring a fluid disposed therein.

As shown in FIG. 1A, the elasticity of the drainage tube 120 allows dependent loops 122 to form, which can lead to urine pooling within the tube 120. Urine pooling within the tube 120 can be a source of CAUTI causing agents, e.g. microbes, bacteria, etc. As shown in FIG. 1B, in an embodiment, a support structure 140 can be configured to engage a portion of the drainage tube 120 and impart rigid or malleable properties thereon. The rigid or malleable properties of the support structure 140 allows a clinician to position the portion of the tube 120 and to provide a consistent negative incline, relative to the desired flow direction. This prevents the formation of dependent loops and prevents fluid pooling within the tube.

In an embodiment, the support structure 140 can be provided as a separate structure from the tube 120. In an embodiment, the support structure 140 can be formed integrally with the tube 120. In an embodiment, the support structure 140 can be provided as part of a kit and can include the tube 120, catheter 110, container 130, catheter placement equipment (e.g. gloves, lubricant, disinfectant, etc.), or combinations thereof.

As shown in FIGS. 2A-2D, in an embodiment, the support structure 140 can be a segmented tube 240, e.g. a ball-and-socket tube. In an embodiment, the segmented tube 240 is provided as a separate structure from the collection system 100, and defines a lumen 224 configured to receive a portion of the tube 120 therein. The segmented tube 240 can impart malleable properties on the portion of the elastic tube 120 disposed therein. In an embodiment, the inner diameter of the lumen 224 is substantially the same, or slightly larger, than the outer diameter of the tube 120 such that the tube fits snugly therein without compromising the patency of the tube lumen 124. In an embodiment, the segmented tube 240 is slidably engaged with the tube 120. In an embodiment, the lumen 224 engages the tube 120 in a friction fit such that the segmented tube 240 is slidable relative to the tube 120 to a position, and remains at that position until it is repositioned. In an embodiment, the segmented tube 240 is integrally formed with the tube 120, for example, the segmented tube 240 can be disposed within a wall of a portion of the elastic tube 120 to impart malleable properties on the portion of the elastic tube 120, as discussed in more detail herein.

In an embodiment, the segmented tube 240 comprises of a plurality of segments 242. Each segment 242 can be formed of a substantially rigid or resilient material such as a metal, plastic, polymer, rubber, or similar suitable material. As shown in FIG. 2D, each segment 242 includes a first portion, or "ball" portion 244, and a second portion, or "socket" portion 246. The ball 244 defines a rounded outer surface 248 and the socket 246 defines a concave receiving surface 250. A radius of curvature of the rounded outer surface 248 of the ball portion 244 is similar to the radius of curvature of the concave receiving surface 250 of the socket portion 246.

As shown in FIG. 2B, a socket 246A of a first segment 242A, is configured to receive the ball 246B of an adjacent, second segment 242B, such that a rounded outer surface 248 of the second segment 242B, contacts the concave receiving surface 250 of the first segment 242A. The interaction between the first segment 242A and the second segment 242B can be a friction fit, interference fit, or press fit engagement, such that the receiving structure 246A can retain the ball 244B therein. Further, the engagement between the first and second segments 242A, 242B, imparts malleable properties on the segmented tube 240 such that a first segment can be positioned relative to a second segment, from a first position to a second position and remain in the second position until it is repositioned.

As shown in FIG. 2C, the ball 244B can rotate within the receiving structure 246A such that an axis 204 of the second segment 242B can be manipulated relative to the axis 202 of the first segment 242A, and remain in the position until it is repositioned. In an embodiment, an axis 202 of the first segment 242A can be positioned at an angle of between 0° and 45°, relative to an axis 204 of the second segment 242B. In an embodiment, an axis 202 of the first segment 242A can be positioned at an angle of between 0° and 10°, relative to an axis 204 of the second segment 242B. As shown in FIG. 2D, each segment 242 of the segmented tube 240 can be orientated relative to each other, which in turn defines the shape of the lumen 224 extending through the segmented tube 240. As such, the configuration of the lumen 224 of the segmented tube 240 imparts a similar shape on the portion of elastic tube 120 disposed therein.

In an embodiment, the segmented tube 240 can be provided as a separate structure from that of the tube 120. The tube 120 can be passed through the lumen 224 and coupled with a catheter 110 and/or collection container 130. In an embodiment, the segmented tube 240 include an elongate slot (not shown) extending axially and communicating with the lumen 224. The elongate slot allows ingress or egress of the tube 120 to/from the lumen 224 in a perpendicular direction to the axis of the lumen 224. Advantageously this allows the segmented tube 240 to be applied to or removed from the tube 120 while the tube 120 is in use. In an embodiment, the segmented tube 240 and the tube 120 is provided as an integrated unit. For example the segmented tube 240 can be attached to an outer surface of the tube, an inner surface of the tube, disposed within a wall of the tube 120, or combinations thereof.

In an exemplary method of use, a segmented tube 240 is provided, as described herein. The tube 120 of an exemplary fluid collection system 100 is disposed within lumen 224 of the segmented tube 240. Optionally the segmented tube 240 can be slid axially relative to the tube 120 until it is positioned with the portion of the tube 120 that is to be manipulated. A user can then bend, twist, or manipulate the segmented tube 240 into a desired position. Worded differently, an axis of a first segment can be manipulated relative to the axis of an adjacent segment until a lumen 224 of the segmented tube 240 is positioned in a desired shape. As such, the shape of the lumen 224 is imparted on the portion of the tube 120. It will be appreciated that the desired shape can include any orientation of straight, curved, helical, or the like, and can include a substantially negative incline relative to a proximal direction of flow, such that a fluid continues to flow through the tube 120 in a proximal direction, to the container 130.

FIGS. 3A-3C show an embodiment of a bi-stable support structure 340, which includes a sheet of bi-stable material. The bi-stable support structure 340 can be made from metal, plastic, polymer, or similar suitable material. In an embodiment, the bi-stable support structure 340 includes two resting states. As shown in FIG. 3A, a first resting state includes an open, extended state 302, defining a substantially rectangular or square shape. As shown in FIG. 3B, a second resting state includes a closed, cylindrical state 304, and defines a lumen 324 extending therethrough.

In an embodiment, the inner diameter of the lumen 324 is substantially the same, or slightly smaller than the outer diameter of the tube 120, such that the tube fits tightly therein, without compromising the patency of the tube lumen 124. In an embodiment, the inner diameter of the lumen 324 is larger than the outer diameter of the tube 120. In an embodiment, the bi-stable support structure 340 is slidably engaged with the tube 120. In an embodiment, the lumen 324 engages the tube 120 in a friction fit such that the bi-stable support structure 340 is slidable relative to the tube 120 to a position, and remains at that position until it is repositioned.

As shown in FIG. 3A, the support structure 340 includes a substantially rectangular shape extending along a plane defined by the longitudinal and lateral axes. For reference, a longitudinal reference line 312 and a lateral reference line 314 are shown as dashed lines. In the extended resting state 302, the support structure 340 includes a slightly curved longitudinal axis. The support structure 340 further includes a proximal edge 342, a first lateral edge 344, a distal edge 346, and a second lateral edge 348. As shown, the proximal edge 342 and the distal edge 346 extend along the lateral axis and as such define a substantially straight shape in the extended orientation 302. The first lateral edge 344 and the second lateral edge 348 extend along the longitudinal axis and as such define a slightly curved shape. In an embodiment, each of the proximal edge 342, the first lateral edge 344, the distal edge 346, and the second lateral edge 348 define substantially the same length. In an embodiment, the proximal edge 342 and distal edge 346 define a first length, and the first lateral edge 344 and second lateral edge 348 define a second length. In an embodiment the first length is less than the second length. In an embodiment, the first length is greater than the second length.

In an embodiment, the support structure 340 can transition between the extended state 302 and the cylindrical state 304 by flexing a lateral length of the extended state 302 transversely. The support structure 340 then becomes biased towards the cylindrical state 304 such that a lateral length of the support structure 340 rolls up and forms a cylinder extending through the longitudinal axis. As shown in FIG. 3B, the cylindrical state 304 defines a lumen 324 and includes a circular proximal edge 342, a circular distal edge 346. The first lateral edge 344 and the second lateral edge 348 extend along a longitudinal axis and transition from a slightly curved shape in the extended state 302, to a substantially straight shape in the cylindrical state 304.

In an embodiment, the first lateral edge 344 extends along an outer surface of the cylinder, and the second lateral edge 348 extends along an inner surface of the lumen 324. It will be appreciated that when transitioning between the extended state 302 and the cylindrical state 304, the bi-stable support structure 340 can roll from an opposite end such that the second lateral edge 348 extends along an outer surface of the cylinder, and the first lateral edge 344 extends along an inner surface of the lumen 324.

In an embodiment, the support structure 340 can roll up to the cylindrical state 304 such that the proximal edge 342 and the distal edge 346 extends through an arc of at least 360°. As shown in FIG. 3B-3C, the proximal edge 342 and the distal edge 346 extends through more than 360° such that a first lateral edge 344 overlaps a second lateral edge 348. As shown in FIG. 3C the first lateral edge 344 can overlap a second lateral edge 348 such that the proximal and distal edges extend through an arc of 540°, 720°, 900°, 1080°, or more, to provide one or more layers of material. Worded differently, the walls of the cylinder can extend through between 1 turn, 1.5 turns, 2 turns, 2.5 turns, or 3 turns, or more to provide one or more layers of the cylinder wall. In an embodiment, the elastic tube 120 can be passed through the lumen 324 and coupled with a catheter 110 and/or collection container 130. In an embodiment, the lumen 324 engages the tube 120 in a friction fit such that the bi-stable support structure 340 is slidable relative to the tube 120 to a position, and remains at that position until it is repositioned.

In an exemplary method of use, a bi-stable support structure 340 is provided, as described herein. In the extended resting state 302, an axial length of a portion of the tube 120 is aligned with the longitudinal axis. The support structure 340 is flexed transversely, through the lateral axis to transition the bi-stable support structure 340 from the expanded state to a cylindrical state 304. The support structure 340 can roll up around the tube 120 and create a support structure lumen 324, through which the tube 120 extends. The cylindrical state 304 defines a straight, rigid lumen 324 extending through the longitudinal axis and imparts a similar shape on the portion of the elastic tube 120 disposed therein. The user can then arrange the support structure 340 at a negative incline relative to the proximal direction, i.e. the desired direction of fluid flow. Advantageously, the bi-stable support structure 340 can be applied or removed from the tube 120 while the tube 120 is in use.

In an embodiment, the support structure includes only a single resting state. For example, as shown in FIGS. 3D-3E a support structure 341 includes a mono-stable material and is bias towards a cylindrical resting state, similar to that shown in FIGS. 3B-3C. The mono-stable support structure 341 can be transitioned from a closed configuration in the cylindrical resting state to an open configuration by unrolling the support structure 341. As noted, the open configuration does not include an expanded resting state and must be held in the open configuration. Worded differently, in both the open and closed positions, the first lateral edge 344 and the second lateral edge 348 maintain a straight configuration, and the proximal edge 342 and the distal edge 346 maintain a curved configuration.

While the support structure 341 is maintained in the open position, an axial length of the tube 120 can be aligned with a longitudinal axis. The support structure 341 can be released and resumes the cylindrical, rolled up configuration, as shown in the FIG. 3D. In the closed configuration, the mono-stable support structure 341 defines a straight rigid lumen 324 that fits tightly about the tube 120 without compromising the patency of the tube lumen 124. The lumen 324 imparts a similar shape on the elastic tube 120, as described herein.

As shown in FIGS. 4A-4C, a support structure 440 includes a jacket that can be fastened about the tube 120 to create a cylinder. The jacket support structure 440 can be made from organic or synthetic material, woven or non-woven material, rubber, neoprene, plastic, polymer, Teflon, nylon, metal, alloy, or similar suitable material. The jacket support structure 440 includes an open configuration 402 (FIG. 4A) and a closed configuration 404 (FIG. 4B). As shown in FIG. 4A, an open configuration 402 defines a substantially rectangular or square shape. As shown in FIG. 4B, a closed configuration 404 defines a cylindrical shape including a lumen 424 extending therethrough.

In an embodiment, an inner diameter of the lumen 424 is substantially the same as the outer diameter of the tube 120 such that the tube fits tightly therein without compromising the patency of the tube lumen 124. In an embodiment, the inner diameter of the lumen 424 is slightly larger than the outer diameter of the tube 120. In an embodiment, the jacket support structure 440 is slidably engaged with the tube 120. In an embodiment, the inner diameter of the lumen 424 is slightly smaller than the outer diameter of the tube 120. In an embodiment, the lumen 424 engages the tube 120 in a friction fit such that the jacket support structure 440 is slidable relative to the tube 120 to a position, and remains at that position until it is repositioned.

As shown in FIG. 4A, the jacket support structure 440 in the open configuration defines a substantially rectangular shape and includes a proximal edge 442, a first lateral edge 444, a distal edge 446, and a second lateral edge 448. The jacket support structure 440 can further include a fastener 450 configured to secure the first lateral edge 444 to the second lateral edge 448. Exemplary fasteners include one or more zips, clasps, latch, hook-and-loop (e.g. VELCRO®), temporary or permanent adhesive, or the like.

Securing the first lateral edge 444 to the second lateral edge 448 transitions the jacket support structure 440 from the open configuration 402 to the closed configuration 404. In the open configuration 402, the jacket support structure 440 can flex through either the longitudinal axis or the lateral axis. In the closed configuration 304 the cylindrical structure inhibits flexion through the longitudinal axis to define a substantially straight, rigid lumen 424. As described herein, the shape of the lumen 424 can impart a similar shape on the elastic tube 120 disposed therein.

In an embodiment, each of the proximal edge 442, the first lateral edge 444, the distal edge 446, and the second lateral edge 448 define substantially the same length. In an embodiment, the proximal edge 442 and distal edge 446 define a first length, and the first lateral edge 444 and second lateral edge 448 define a second length. In an embodiment the first length is less than the second length. In an embodiment, the first length is greater than the second length.

In an exemplary method of use, a jacket support structure 440 is provided, as described herein. In the open configuration 402, an axial length of a portion of the tube 120 is aligned with the longitudinal axis. The support structure 440 is flexed transversely, through the lateral axis to transition the jacket support structure 440 from the open configuration to a closed configuration 404. A fastener 450 can secure the support structure 440 in the closed configuration 404. The support structure 440 creates a support structure lumen 424, through which a portion of the elastic tube 120 extends. The cylindrical state 404 defines a straight, rigid lumen 424, extending through the longitudinal axis and can fit tightly about the tube 120 to impart a similar shape on the portion of the tube 120. The user can then arrange the support structure 440 at a negative incline relative to a proximal flow direction, i.e. a desired direction of fluid flow. Advantageously, the jacket support structure 440 can be applied or removed from the tube 120 while the tube 120 is in use.

Figure 5A:
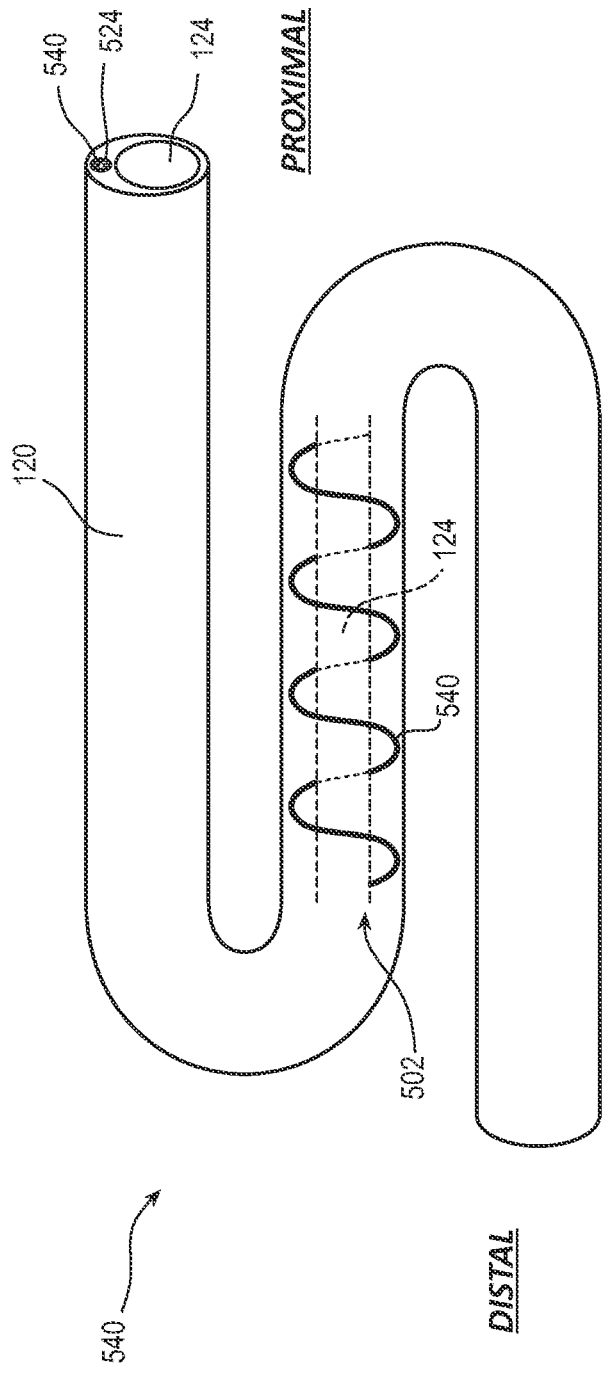
FIG. 5A shows a perspective view of a drainage tube including a malleable support structure, in accordance with embodiments disclosed herein.
Figure 5B:
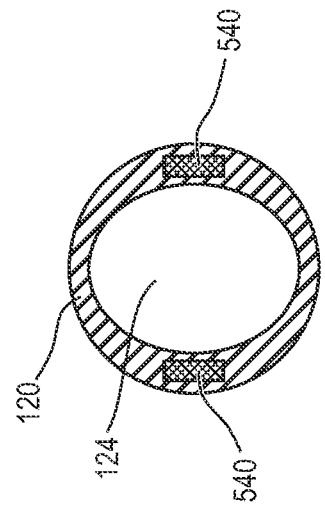
FIGS. 5B-5D show a lateral cross-sectional view of a drainage tube including a malleable support structure, in accordance with embodiments disclosed herein.
Figure 5C:
Figure 5D:
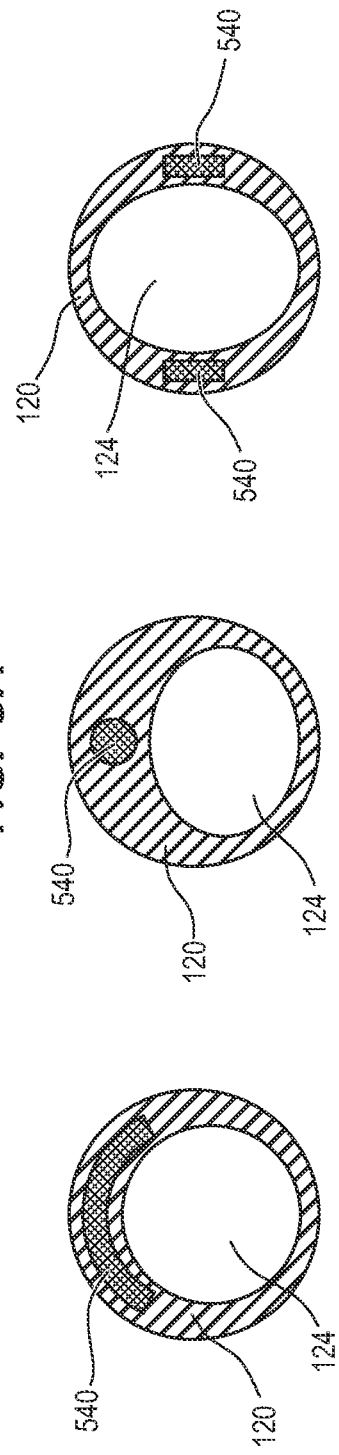

As shown in FIGS. 5A-5D, a tube 120 includes a malleable support structure 540 formed integrally with at least a portion of the tube 120. The malleable support structure 540 can be a malleable wire extending through a wall of the tube 120. The malleable support structure 540 can be formed of a malleable material such as metal, alloy, nitinol, plastic, polymer, combinations thereof or the like. A cross sectional area of the malleable support structure 540 can define a circular shape, rectangular shape, curved rectangle shape, or the like, although other closed curve polygonal shapes are also contemplated. In an embodiment, as shown in FIG. 5D, two or more malleable support structures 540 can extend through the wall of the tube 120. In an embodiment, the malleable support structure 540 can extend through the wall of the tube 120 in a spiral or helical shape, encircling the tube lumen 124.

In an embodiment, the malleable support structure 540 can be co-extruded with the tube 120 as an integrated structure. In an embodiment, the tube 120 includes a drainage lumen 124 and a support structure lumen 524, into which the malleable support structure 540 can be disposed. The malleable support structure 540 imparts malleable properties on the tube 120 such that the tube 120 can be manipulated into a desired shape. For example the tube 120 can be manipulated to a coiled or folded position such as shown in FIG. 5A, or to maintain a consistent negative incline relative to the desired proximal flow direction.

In an embodiment, the tube 120 includes one or more support structure lumen(s) 524 extending through a side wall as described herein. The support structure lumen 524 can be in fluid communication with a pump device configured to fill the support structure lumen 524 with an inflation fluid (e.g. gas or liquid). The pump device can compress the inflation fluid within the support structure lumen 524 to provide a turgid state. The turgid support structure lumen(s) 524 provides a substantially rigid structure to support the tube 120, and transitions the elastic tube 120 from a relaxed state to a rigid state. With the tube 120 in a rigid state, the tube 120 can be positioned to provide a consistent negative incline. In an embodiment, the pump device can alternately compress and release the inflation fluid to/from the support structure lumen(s) 524 to "pulse" the tube 120 between a relaxed state and a rigid state. As such, a fluid disposed within the drainage lumen 124 can be "pulsed" through the tube 120 and dislodge any dependent loops or air locks disposed within the drainage lumen 124.

Figure 6:
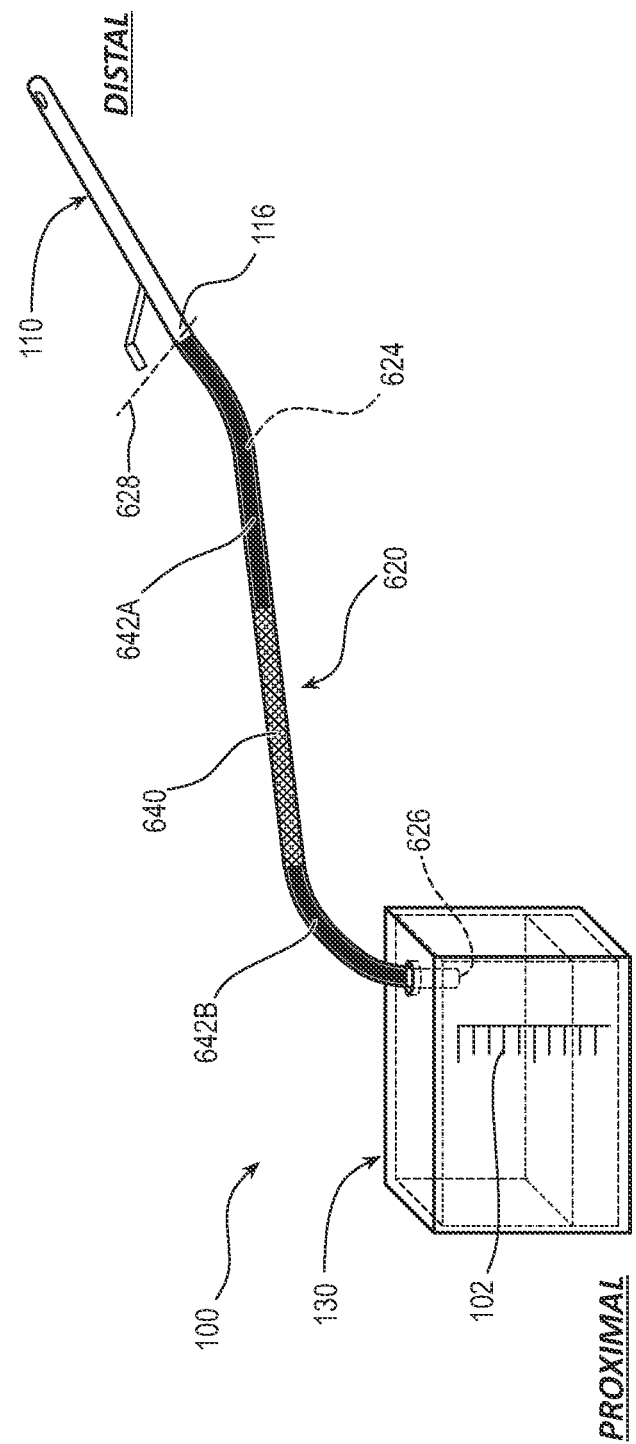
FIG. 6 shows a fluid collection system including a tube including portions displaying differing mechanical properties, in accordance with embodiments disclosed herein.

As shown in FIG. 6, a fluid collection system 100 includes a tube 620 that defines a lumen 624 and provides fluid communication between a catheter 110 and a collection container 130. In an embodiment, the tube 620 can be formed integrally, as a single structure, and comprises two materials that can display different mechanical properties. The tube 620 includes a first, support structure, portion 640, including a first material, and a second, connector portion 642, including of a second material. In an embodiment, the first material can display rigid or malleable properties and can include plastic, polymer, high density polyethylene (HDPE), nylon, metal, alloy, combinations thereof, or the like. In an embodiment, the second material can display malleable or elastic properties and can include plastic, polymer, Polyvinyl chloride (PVC), silicone, rubber, combinations thereof, or the like.

In an embodiment, the support structure 640 can be disposed towards a proximal end of the tube 620. In an embodiment, the support structure 640 extends from a proximal end 626 to a point proximal of the distal end 628 of the tube 620. In an embodiment, the connector portion 642 can be disposed towards a distal end of the tube 620. In an embodiment, the connector portion 642 extends from the distal end 628 to a point distal of the proximal end 626 of the tube 620. In an embodiment, the support structure 640 can extend along a mid-section of the tube 620 and include a first connector portion 642A disposed towards a distal end and a second connector portion 642B towards a proximal end. In an embodiment, the fluid collection system 100 can include one or more support structures 640. In an embodiment, the tube 620 can include two or more support structures 640, with one or more connector portions 642 disposed therebetween.

In an embodiment, the support structure 640 can be positioned from a first position to a second position and remain in the second position until it is repositioned. As such the support structure(s) 640 can be arranged in a folded or helical arrangement to maintain a consistent negative incline between the catheter 110 and the collection container 130.

Advantageously the tube 620 provides a relatively flexible connector portion between the support structure 640 and the catheter 110, and optionally between the support structure 640 and the container 130 to provide patient comfort and allow the patient to move. The tube 620 also provides a relatively malleable, or rigid, support structure 640 that can be positioned to provide a consistent negative incline and maintain a proximal flow. In an embodiment, the tube 620 can be provided as a modular tube including one or more support structure(s) 640 and relatively flexible, second portion(s) 642 that can be coupled together in various combinations to provide fluid communication between the catheter 110 and the container 130. As such, the length of the support structure(s) 640 can be modified to suit a desired length.

Figure 7C:
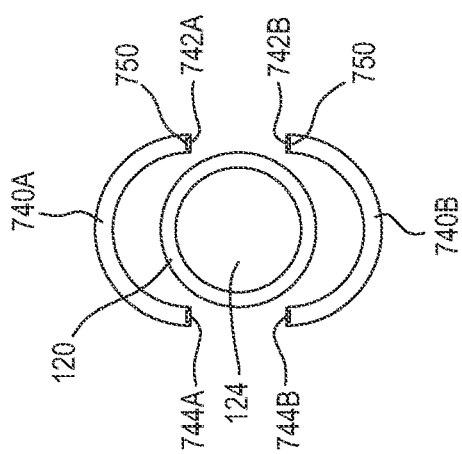
FIG. 7C show a lateral cross-sectional view of a magnetic support structure, in accordance with embodiments disclosed herein.
Figure 7A:
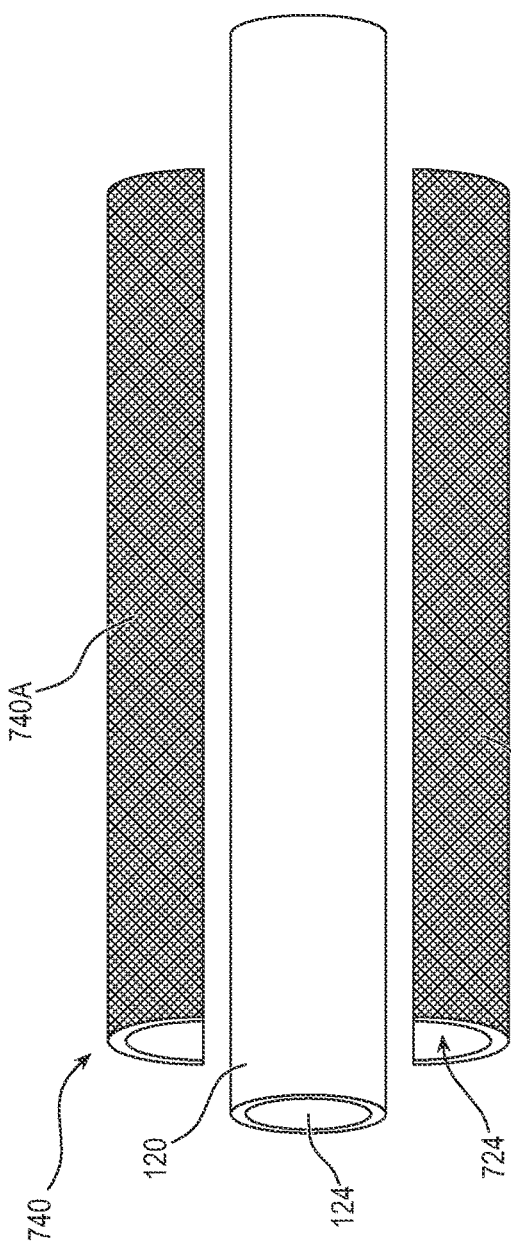
FIGS. 7A-7B show a perspective view of a magnetic support structure, in accordance with embodiments disclosed herein.
Figure 7B:
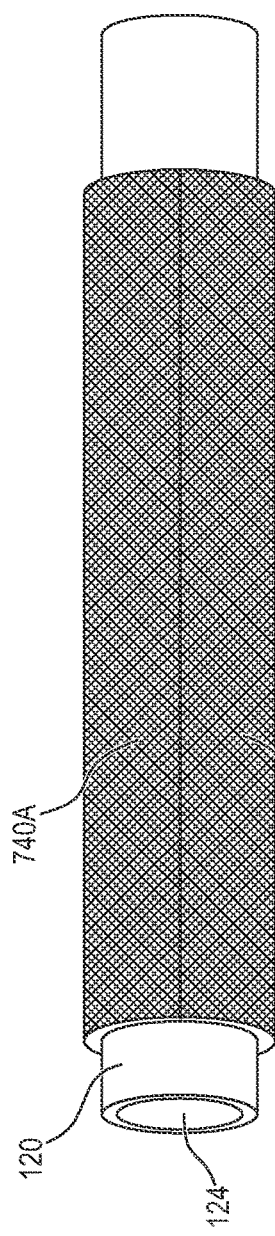

As shown in FIGS. 7A-7C, in an embodiment, a magnetic support structure 740 is provided. The magnetic support structure 740 can be separated longitudinally into two or more portions, e.g. a first half 740A and a second half 740B. Advantageously this allows the magnetic support structure 740 to be applied to or removed from the tube 120 while the tube 120 is in use. Each of the first and second portions 740A, 740B extend through an arc such that together the support structure 740 encircles the tube 120. For example, each of the first and second portions 740A, 740B extend through an arc of 180°. Similarly, in an embodiment, the support structure 740 can include three portions (not shown), each extending through an arc of arc of 120°. It will be appreciated, however, that the two or more portions can extend through arcs that are of equal sizes or are of different sizes.

Each of the first and second portions 740A, 740B, include a first contact surface 742 extending longitudinally along a first side of the support structure 740, and a second contact surface 742B extending longitudinally along a second side of the support structure 740. When the support structure 740 is assembled, a first contact surface 742A of the first portion 740A engages a first contact surface 742B of the second portion 740B. Similarly a second contact surface 744A of the first portion 740A engages a second contact surface 744B of the second portion 740B.

In an embodiment, each of the first and second contact surfaces 742, 744, include one or more magnets 750 inset into the first and second contact surfaces 742, 744, such that a surface of the magnet is flush with the surface of the contact surface. Further, magnets on opposing contacts surfaces are configured to attract each other such that the first and second portions 740A, 740B are secured to one another. In an embodiment, one of the first contact surface 742 or the second contact surface 744, can include a hinge joining the first portion 740A with the second portion 740B. As such, the first and second portions 740A, 740B, can pivot about the hinge between and open and a closed configuration. Further, the magnets 750 disposed within the opposite contact surface from the hinge can secure the magnetic support structure 740 in a closed configuration.

As shown in FIGS. 7A-7B, in an assembled state, the support structure 740 defines a lumen 724. An inner diameter of the lumen 724 can be substantially the same as an outer diameter of the elastic tuber 120 such that the tube 120 fits snugly therein. In an embodiment, the support structure 740 can be formed of a substantially rigid, or malleable material, for example, plastic, polymer, high density polyethylene (HDPE), nylon, metal, alloy, combinations thereof, or the like. When assembled, the support structure 740 defines a lumen 724 that can impart rigid or malleable properties on the portion of the elastic tube 120 disposed therein. In an embodiment the support structure 740 causes the tube 120 to assume the same shape as the shape of the lumen 724. For example, as shown in FIGS. 7A-7B, the lumen 724 defines a substantially straight shape extending longitudinally and, when assembled, causes the tube 120 to adopt the same shape as the lumen 724. It will be appreciated that the shape of the lumen 724 can include other shapes such as bent, curved, helical, or the like and will cause the tube 120 to adopt a similar shape.

As shown in FIGS. 8A-8E, in an embodiment a magnetic peristalsis device 840 is provided. The magnetic peristalsis device 840 can be separated longitudinally in to two or more portions, e.g. a first portion 840A and a second portion 840B. Advantageously this allows the magnetic support structure 740 to be applied to, or removed from, the tube 120 while the tube 120 is in use. Each of the first and second portions 840A, 840B extend through an arc such that together the peristalsis device 840 encircles the tube 120. For example, each of the first and second portions 840A, 840B extend through an arc of 180°. Alternatively, the peristalsis device 840 can include three portions (not shown), each extending through an arc of arc of 120°. It will be appreciated, however, that the two or more portions can extend through arcs that are of equal sizes or are of different sizes.

Each of the first and second portions 840A, 840B, include a first contact surface 842 extending longitudinally along a first side of the peristalsis device 840, and a second contact surface 842B extending longitudinally along a second side of the peristalsis device 840. When the peristalsis device 840 is assembled, a first contact surface 842A of the first portion 840A engages a first contact surface 842B of the second portion 840B. Similarly a second contact surface 844A of the first portion 840A engages a second contact surface 844B of the second portion 840B.

In an embodiment, each of the first and second contact surfaces 842, 844, include one or more magnets 850 inset into the first and second contact surfaces 842, 844, such that a surface of the magnet is flush with the surface of the contact surface. Further, the magnets on opposing contacts surfaces are configured to attract each other such that the first and second portions 840A, 840B are secured to each another.

In an embodiment, one of the first contact surface 842 or the second contact surface 844, can include a hinge joining the first portion 840A with the second portion 840B. As such, the first and second portions 840A, 840B, can pivot about the hinge between and open and a closed configuration. Further, the magnets 850 disposed within the contact surface opposite the hinge can secure the peristalsis device 840 in a closed configuration.

Figure 8C:
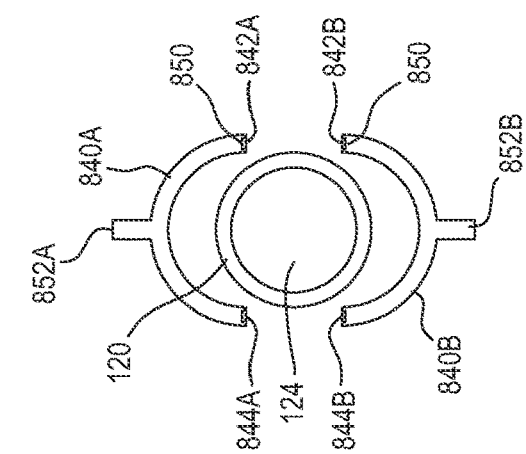
FIG. 8C show a lateral cross-sectional view of a magnetic peristalsis device, in accordance with embodiments disclosed herein.
Figure 8A:
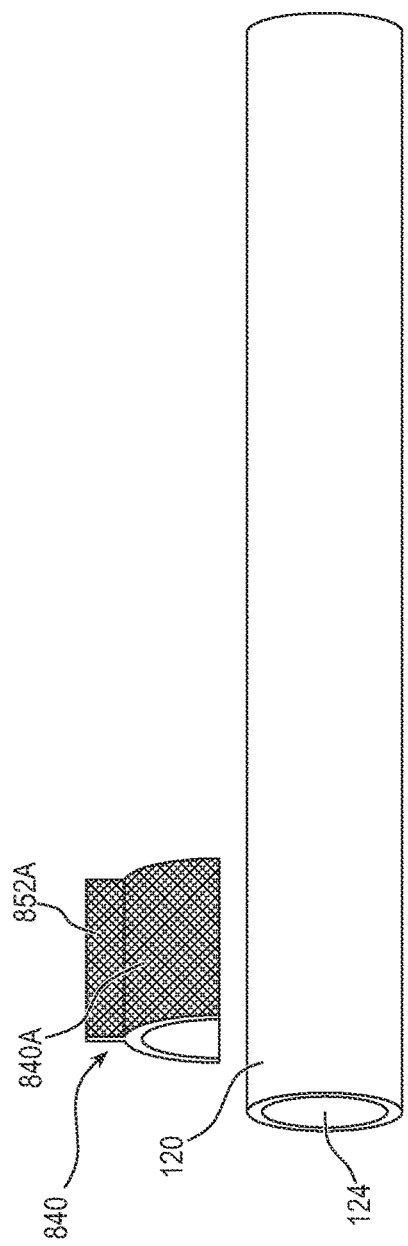
FIGS. 8A-8B show a perspective view of a magnetic peristalsis device, in accordance with embodiments disclosed herein.
Figure 8B:
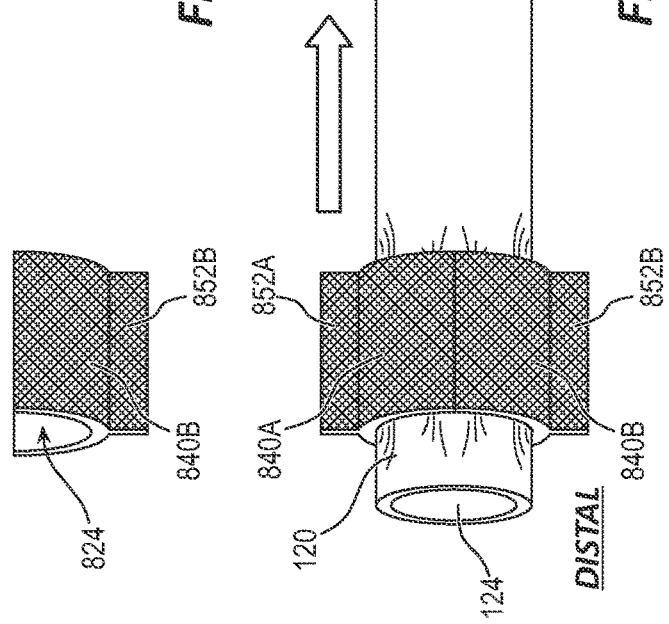

As shown in FIGS. 8A-8B, in an assembled state, the peristalsis device 840 defines a lumen 824. An inner diameter of the lumen 824 can be smaller than an outer diameter of the elastic tube 120, such that the patency of the lumen 124 is compromised, constricting a cross-sectional area of the lumen 124. In an embodiment, the peristalsis device 840 can be urged proximally along the tube 120, constricting consecutive portions of the lumen 124 as the tube passed through the peristalsis device. This urges any fluid disposed within the lumen in a proximal direction towards the container 130. In an embodiment, an inner surface of the lumen 824 includes one or more coatings to facilitate the sliding movement, or to promote urine flow within lumen 124. Exemplary coatings can include low friction, hydrophilic, hydrophobic properties, combinations thereof, or the like.

Figure 8F:
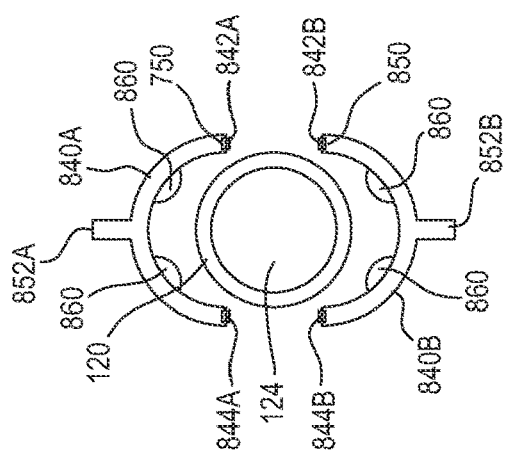
FIG. 8F show a lateral cross-sectional view of a magnetic peristalsis device including rollers, in accordance with embodiments disclosed herein.
Figure 8D:
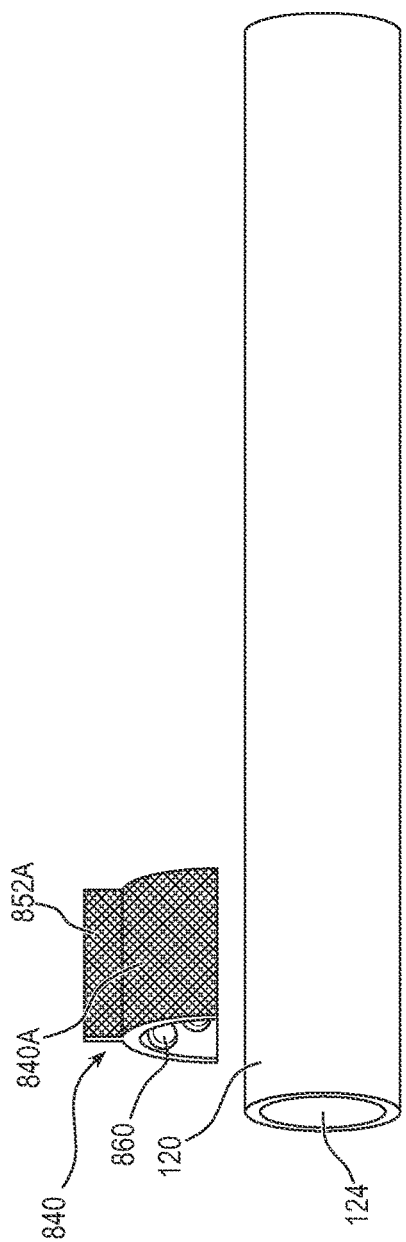
FIGS. 8D-8E show a perspective view of a magnetic peristalsis device including rollers, in accordance with embodiments disclosed herein.
Figure 8E:
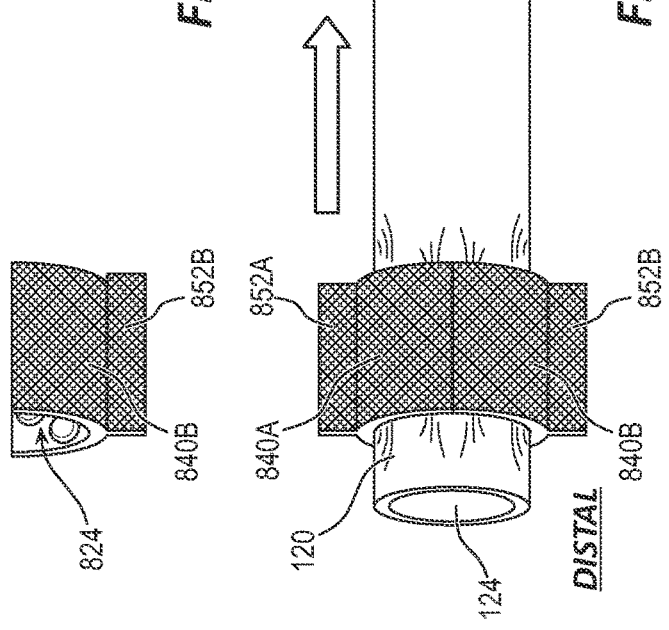

As shown in FIGS. 8D-8F, in an embodiment, an inner surface of the lumen 824 includes one or more rollers 860, for example wheels, ball bearings, or similar structures. The rollers 860 can be inset into the inner surface of the lumen 824. In an embodiment, the rollers 860 can constrict, or further constrict, the tube lumen 124 to facilitate moving fluid through the lumen 124, when in a closed configuration. In an embodiment, the rollers 860 reduce friction between inner surface of the lumen 824 and the outer surface of the tube 120 to facilitate urging the peristalsis device 840 along the tube 120.

In an embodiment, one or more rollers 860 can be coupled with a motor, a power source, and/or controls (not shown), which are configured to rotate the rollers 860 and urge the peristalsis device 840 along the tube 120, without requiring a user to urge the device along the tube. The controls can include, for example, one or more switches, sensors, or the like, that control the motor and/or power source.

In an embodiment, peristalsis device 840 can be formed of a substantially rigid, or resilient material, for example, plastic, polymer, high density polyethylene (HDPE), nylon, metal, alloy, combinations thereof, or the like. In an embodiment the peristalsis device 840 can include one or more handles 852. For example, a first handle 852A extending from the first portion 840A, and, a second handle 852B extending from the second portion 840B. The handles 852 can facilitate grasping the peristalsis device 840, transitioning the peristalsis device 840 between an open and a closed configuration, or urging the peristalsis device 840 along the tube 120, or combinations thereof.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A drainage system, comprising:
a drainage tube configured to drain urine from a body of a patient; and
a support structure defining a central lumen configured to receive a portion of the drainage tube through an elongate slot in the support structure, the support structure including a plurality of segments, each segment of the plurality of segments including a ball portion and a socket portion, the socket portion defining an outer rim encircling a central axis of the central lumen, a first segment of the plurality of segments engaging an adjacent segment in a friction fit engagement while simultaneously configured to allow ingress or egress of the portion of the drainage tube through the elongate slot, such that the first segment is positionable relative to the adjacent segment to define a shape of the central lumen, impart the shape on the portion of the drainage tube disposed therein, and prevent the urine from pooling in dependent loops in the portion of the drainage tube disposed in the central lumen, thereby mitigating catheter-associated urinary tract infections.

2. The drainage system according to claim 1, wherein the plurality of segments are positionable such that the first segment is positioned from a first position to a second position, and remains in the second position until the first segment is repositioned.

3. The drainage system according to claim 1, wherein the socket portion of the first segment is configured to engage the ball portion of the adjacent segment in the friction fit engagement.

4. The drainage system according to claim 1, wherein an inner surface of the central lumen engages an outer surface of the drainage tube and is configured to allow the support structure to be slidable along an axis of the drainage tube to a position, and remain at the position until repositioned.

5. The drainage system according to claim 1, wherein a central axis of the first segment is positioned at an angle, relative to a central axis of the adjacent segment, of between 0° and 45°.

6. The drainage system according to claim 1, wherein a distal end of the drainage tube is in fluid communication with a catheter and a proximal end of the drainage tube is in fluid communication with a collection container.

7. The drainage system according to claim 1, wherein the elongate slot allows the portion of the drainage tube to be received or removed from the support structure while the drainage tube is being used to drain urine from the body of the patient.

8. The drainage system according to claim 1, wherein the ball portion of each segment of the plurality of segments is discontinuous, and aligns with a discontinuous socket portion of the adjacent segment of the plurality of segments thereby forming the elongate slot.

9. The drainage system according to claim 1, wherein each segment of the plurality of segments is formed as a monolithic piece.

10. The drainage system according to claim 1, wherein each segment of the plurality of segments extends continuously through more than 180° between a first edge of the elongate slot through to a second edge of the elongate slot, the first edge of the elongate slot disposed opposite the second edge of the elongate slot.

\* \* \* \* \*